United States Patent [19]

Komurasaki et al.

[11] Patent Number: 5,523,391

[45] Date of Patent: Jun. 4, 1996

[54] DNA FRAGMENT ENCODING TUMOR CELL GROWTH INHIBITORS

[75] Inventors: Toshi Komurasaki; Hitoshi Toyoda; Makoto Yoshimoto; Kazunori Hanada, all of Tokyo, Japan

[73] Assignee: Taisho Pharmaceutical Co., Ltd., Japan

[21] Appl. No.: 244,309

[22] PCT Filed: Dec. 3, 1992

[86] PCT No.: PCT/JP92/01580

§ 371 Date: May 25, 1994

§ 102(e) Date: May 25, 1994

[87] PCT Pub. No.: WO93/11233

PCT Pub. Date: Jun. 10, 1993

[51] Int. Cl.$^6$ .......................... C12N 15/28; C12N 15/19; C12N 15/12

[52] U.S. Cl. .................. 536/23.5; 536/23.1; 530/324; 435/69.1; 435/172.3; 435/320.1; 435/252.3

[58] Field of Search .................. 536/23.1, 23.5; 530/324; 435/69.1, 172.3, 320.1, 252.3

[56] References Cited

U.S. PATENT DOCUMENTS

| | | | |
|---|---|---|---|
| 4,675,285 | 6/1987 | Clark et al. | 435/6 |
| 5,281,520 | 1/1994 | O'Hara et al. | 435/69.1 |
| 5,384,394 | 1/1995 | Komurasaki et al. | 530/324 |

OTHER PUBLICATIONS

C. C. Lee et al. Science 239:1288–1291 (Mar. 1988).
J. M. Wozney Meth. in Enzymol. 182:738–751 (1990).
J. Cell Physiol., vol. 119, 1984, pp. 101–106 Harel et al.

*Primary Examiner*—Robert A. Wax
*Assistant Examiner*—Rebecca Prouty
*Attorney, Agent, or Firm*—Lorusso & Loud

[57] ABSTRACT

DNA fragments encoding a tumor cell growth inhibitors and having a nucleotide sequence shown by formula (1) below, which are produced by preparing cDNA library from mRNA of the established 3T3 cell-derived cell line, amplifying various DNA fragments considered to encode the tumor cell growth inhibitors by the PCR method, analyzing the nucleotide sequences of these DNA fragments and determining the nucleotide sequences of the DNA fragments encoding the inhibitors:

```
                                        27
GTG CAG ATT ACA AAG TGT AGT TCT GAC ATG
                                        54
GAC GGC TAC TGC TTG CAT GGC CAG TGC ATC
                                        81
TAC CTG GTG GAC ATG AGA GAG AAA TTC TGC
                                       108
AGA TGT GAA GTG GGC TAC ACT GGT CTG CGA
TGT GAG CAC X .......... (1)
``` wherein X represents TTC TTT CTA or TTC (SEQ ID NO:1 or SEQ ID NO:2).

1 Claim, 10 Drawing Sheets

FIG. 3

OLIGONUCLEOTIDES USED AS PRIMERS IN THE
PCR METHOD

OLIGONUCLEOTIDE ①
  5' - G T A C A A A T A A C A A A A T G - 3'
          T    G      T      T      G
          G          C      G
          C                    C

OLIGONUCLEOTIDE ②
  5' - A A A A A A A A A T G T T C A C A - 3'
          G G  G    G    C    G

OLIGONUCLEOTIDE ③
  5' - G T A T A A C C A A C T T C A C A - 3'
          G    T      T    C    G
          G         G
          C         C

OLIGONUCLEOTIDE ④
  5' - T A G T T C T G A C A T G G A C G G C T - 3'

OLIGONUCLEOTIDE ⑤
  5' - T G G A C A T G A G A G A G A A A T T C - 3'

OLIGONUCLEOTIDE ⑥
  5' - A T G A G T A T T T C T T C C A G G G - 3'

OLIGONUCLEOTIDE ⑦
  5' - A G C C G T C C A T G T C A G A A C T A - 3'

OLIGONUCLEOTIDE ⑧
  5' - G A A T T T C T C T C T C A T G T C C A - 3'

OLIGONUCLEOTIDE ⑨
  5' - A G C A A G T T C A G C C T G G T T A A - 3'

OLIGONUCLEOTIDE ⑩
  5' - G T G C A G A T T A C A A A G T G T A G - 3'

OLIGONUCLEOTIDE ⑪
  5' - T A G A A A G A A G T G C T C A C A T C - 3'

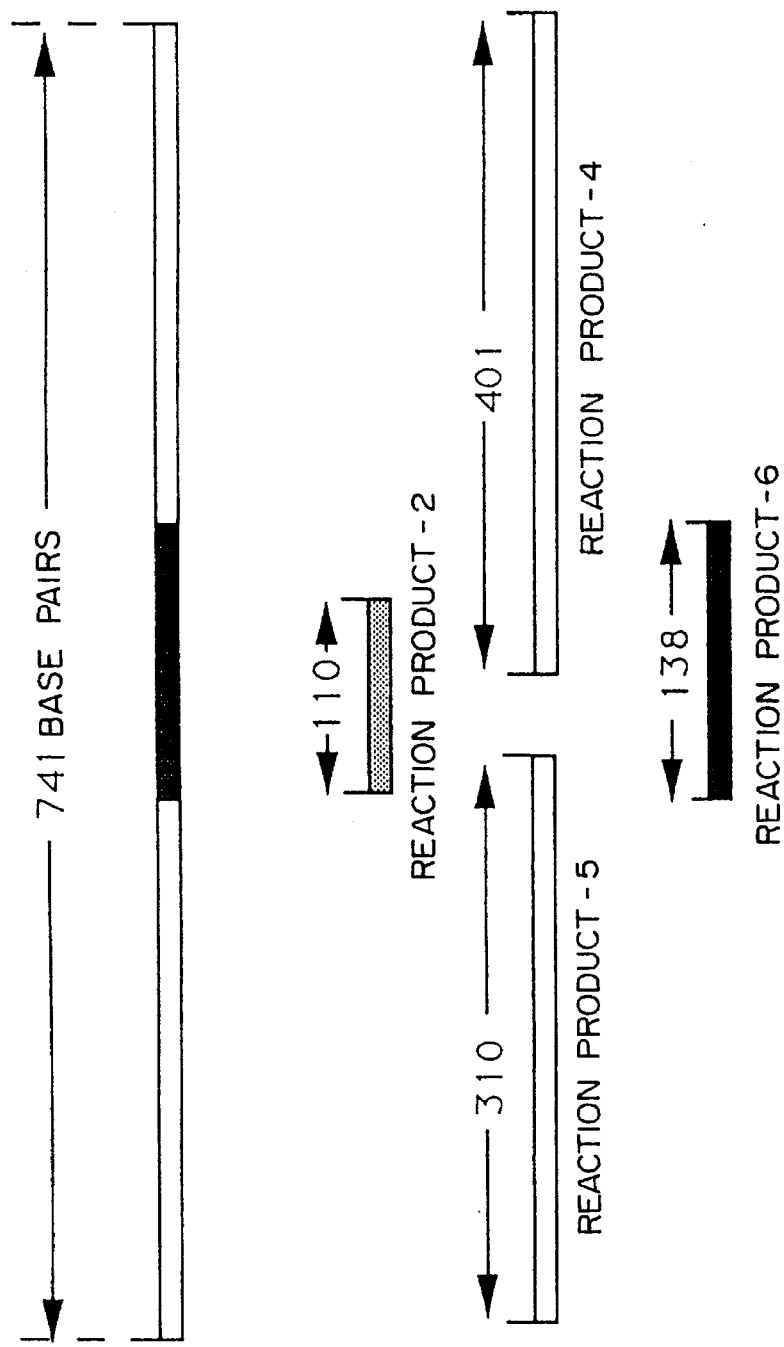

FIG. 6

```
                                                                        54
GTG CAG ATT ACA AAG TGT AGT TCT GAC ATG GAC GGC TAC TGC TTG CAT GGC CAG
Val Gln Ile Thr Lys Cys Ser Ser Asp MET Asp Gly Tyr Cys Leu His Gly Gln

108
TGC ATC TAC CTG GTG GAC ATG AGA GAG AAA TTC TGC AGA TGT GAA GTG GGC TAC
Cys Ile Tyr Leu Val Asp MET Arg Glu Lys Phe Cys Arg Cys Glu Val Gly Tyr

AC
```

NUCLEOTIDE SEQUENCE OF DNA FRAGMENT ENCODING A PART OF P-1 AND THE AMINO ACID SEQUENCE DEDUCED THEREFROM

FIG. 7

```
           11           20           29           38           47
TG GAC ATG AGA GAG AAA TTC TGC AGA TGT GAA GTG GGC TAC ACT GGT CTG CGA
   Asp MET Arg Glu Lys Phe Cys Arg Cys Glu Val Gly Tyr Thr Gly Leu Arg 56           65           74           83           92          101
TGT GAG CAC TTC TTT CTA ACT GTT CAC CAA CCC TTG AGC AAA GAA TAC GTT GCG
Cys Glu His Phe Phe Leu Thr Val His Gln Pro Leu Ser Lys Glu Tyr Val Ala 110          119          128          137          146          155
TTG ACA GTG ATT CTC ATT TTC CTG TTT CTC ATC ATA ACC GCT GGA TGC ATA TAC
Leu Thr Val Ile Leu Ile Phe Leu Phe Leu Ile Ile Thr Ala Gly Cys Ile Tyr 164          173          182          191          200          209
TAT TTC TGC AGA TGG TAC AAA AAT CGA AAA AGT AAA AAA TCG AGG GAG GAA TAT
Tyr Phe Cys Arg Trp Tyr Lys Asn Arg Lys Ser Lys Lys Ser Arg Glu Glu Tyr 218          227          236          245          254         267          277
GAG AGA GTG ACC TCA GGG GAC CCA GTG CTG CCA CAG GTC TGA ACAGTGCCAT CAAGTTACGG
Glu Arg Val Thr Ser Gly Asp Pro Val Leu Pro Gln Val 287          297          307          317          327          337          347

ACAAGGATTC ACAGTGTGCC TGGCTGATGT CAATATTTTC TCATGTTAAT AATATTTATG TTGGGTCATC 357          367          377          387          397

TGTTAGGTCA ATAACTATAT TTTTAATACA ATTGGAAAGT GTTTTATTTT TGAC
```

NUCLEOTIDE SEQUENCE OF DNA FRAGMENT ENCODING
THE C-TERMINAL REGION OF P-1 AND THE AMINO
ACID SEQUENCE DEDUCED THEREFROM

FIG. 8

```
                          27                                                    54
GCG ACT TGG TGG GCT CTG GTA CCT GGA TCA GCT CGG TTC CAA CTC AGC CAC AGG
Ala Thr Trp Trp Ala Leu Val Pro Gly Ser Ala Arg Phe Gln Leu Ser His Arg 81                                                   108
CAC CTT GCT CCC GCC GGC CGC CGC GCA CTC CGC AAG CTG CAC CGA GAA AGA AGG
His Leu Ala Pro Ala Gly Arg Arg Ala Leu Arg Lys Leu His Arg Glu Arg Arg 135                                                   162
ATG GAG ACG CTC CCT GCC TCT TGG GTC TTG ACG CTG CTT TGT CTA GGT TCC CAC
MET Glu Thr Leu Pro Ala Ser Trp Val Leu Thr Leu Leu Cys Leu Gly Ser His 189                                                   216
CTT CTA CAG GCA GTT ATC AGC ACA ACC GTG ATC CCA TCA TGC ATC CCA GGA GAA
Leu Leu Gln Ala Val Ile Ser Thr Thr Val Ile Pro Ser Cys Ile Pro Gly Glu 243                                                   270
TCC GAG GAT AAC TGT ACC GCC TTA GTT CAG ATG GAA GAC GAT CCC CGT GTG GCT
Ser Glu Asp Asn Cys Thr Ala Leu Val Gln MET Glu Asp Asp Pro Arg Val Ala

297
CAA GTG CAG ATT ACA AAG TGT AGT TCT GAC ATG GAC GGC T
Gln Val Gln Ile Thr Lys Cys Ser Ser Asp MET Asp Gly
```

NUCLEOTIDE SEQUENCE OF DNA FRAGMENT ENCODING THE N-TERMINAL REGION OF P-1 AND THE AMINO ACID SEQUENCE DEDUCED THEREFROM

138 BASE PAIRS →

ELECTROPHORESIS OF THE REACTION PRODUCT 6 ON 5% POLYACRYLAMIDE GEL

FIG. 10

```
                                                                    54
GTG CAG ATT ACA AAG TGT AGT TCT GAC ATG GAC GGC TAC TGC TTG CAT GGC CAG
Val Gln Ile Thr Lys Cys Ser Ser Asp MET Asp Gly Tyr Cys Leu His Gly Gln

108
TGC ATC TAC CTG GTG GAC ATG AGA GAG AAA TTC TGC AGA TGT GAA GTG GGC TAC
Cys Ile Tyr Leu Val Asp MET Arg Glu Lys Phe Cys Arg Cys Glu Val Gly Tyr

135
ACT GGT CTG CGA TGT GAG CAC TTC TTT CTA
Thr Gly Leu Arg Cys Glu His Phe Phe Leu
```

NUCLEOTIDE SEQUENCE OF DNA FRAGMENT ENCODING THE ENTIRE REGION OF P-1 AND THE AMINO ACID SEQUENCE DEDUCED THEREFROM

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 138 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GTGCAGATTA  CAAAGTGTAG  TTCTGACATG  GACGGCTACT  GCTTGCATGG  CCAGTGCATC         60

TACCTGGTGG  ACATGAGAGA  GAAATTCTGC  AGATGTGAAG  TGGGCTACAC  TGGTCTGCGA        120

TGTGAGCACT  TCTTTCTA                                                          138
```

( 2 ) INFORMATION FOR SEQ ID NO:2:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GTGCAGATTA  CAAAGTGTAG  TTCTGACATG  GACGGCTACT  GCTTGCATGG  CCAGTGCATC         60

TACCTGGTGG  ACATGAGAGA  GAAATTCTGC  AGATGTGAAG  TGGGCTACAC  TGGTCTGCGA        120

TGTGAGCACT  TC                                                                132
```

( 2 ) INFORMATION FOR SEQ ID NO:3:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Val  Gln  Ile  Thr  Lys  Cys  Ser  Ser  Asp  Met  Asp  Gly  Tyr  Cys  Leu  His
 1              5                        10                       15

Gly  Gln  Cys  Ile  Tyr  Leu  Val  Asp  Met  Arg  Glu  Lys  Phe  Cys  Arg  Cys
              20                        25                       30

Glu  Val  Gly  Tyr  Thr  Gly  Leu  Arg  Cys  Glu  His  Phe  Phe  Leu
              35                        40                       45
```

( 2 ) INFORMATION FOR SEQ ID NO:4:

( i ) SEQUENCE CHARACTERISTICS:

(A) LENGTH: 44 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:4:

| Val | Gln | Ile | Thr | Lys | Cys | Ser | Ser | Asp | Met | Asp | Gly | Tyr | Cys | Leu | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Gln | Cys | Ile | Tyr | Leu | Val | Asp | Met | Arg | Glu | Lys | Phe | Cys | Arg | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Glu | Val | Gly | Tyr | Thr | Gly | Leu | Arg | Cys | Glu | His | Phe |
|-----|-----|-----|-----|-----|-----|-----|-----|-----|-----|-----|-----|
|     |     | 35  |     |     |     |     | 40  |     |     |     |     |

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:5:

TAGTTCTGAC ATGGACGGCT                                                                           20

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:6:

TGGACATGAG AGAGAAATTC                                                                           20

(2) INFORMATION FOR SEQ ID NO:7:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:7:

ATGAGTATTT CTTCCAGGG                                                                            19

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:8:

AGCCGTCCAT GTCAGAACTA                                                                           20

(2) INFORMATION FOR SEQ ID NO:9:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:9:

GAATTTCTCT CTCATGTCCA                                               20

( 2 ) INFORMATION FOR SEQ ID NO:10:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:10:

AGCAAGTTCA GCCTGGTTAA                                               20

( 2 ) INFORMATION FOR SEQ ID NO:11:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:11:

GTGCAGATTA CAAAGTGTAG                                               20

( 2 ) INFORMATION FOR SEQ ID NO:12:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:12:

TAGAAAGAAG TGCTCACATC                                               20

( 2 ) INFORMATION FOR SEQ ID NO:13:

( i ) SEQUENCE CHARACTERISTICS:
      ( A ) LENGTH: 53 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:13:

TGGACATGAG AGAGAAATTC TGCAGATGTG AAGTGGGCTA CACTGGTCTG CGA          53

( 2 ) INFORMATION FOR SEQ ID NO:14:

( i ) SEQUENCE CHARACTERISTICS:
      ( A ) LENGTH: 17 amino acids
      ( B ) TYPE: amino acid
      ( C ) STRANDEDNESS: single (D) TOPOLOGY: linear (ii) MOLECULE TYPE: peptide (xi) SEQUENCE DESCRIPTION: SEQ ID NO:14:

Asp Met Arg Glu Lys Phe Cys Arg Cys Glu Val Gly Tyr Thr Gly Leu
1               5                   10                  15
Arg (2) INFORMATION FOR SEQ ID NO:15:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:15:

GCGACTTGGT GGGCTCTGGT ACCTGGATCA GCTCGGTTCC AACTCAGCCA CAGG    54

(2) INFORMATION FOR SEQ ID NO:16:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:16:

Ala Thr Trp Trp Ala Leu Val Pro Gly Ser Ala Arg Phe Gln Leu Ser
1               5                   10                  15
His Arg

DNA FRAGMENT ENCODING TUMOR CELL GROWTH INHIBITORS

TECHNICAL FIELD

The present invention relates to DNA fragments encoding novel tumor cell growth inhibitors. More particularly, the present invention relates to DNA fragments encoding novel tumor cell growth factors which can be obtained from the culture supernatant of 3T3 cell-derived cell line and exhibit an activity of inhibiting the growth of tumor cells.

BACKGROUND ART

Synthetic drugs such as chemotherapeutic agents or immunotherapeutic agents have been heretofore widely used as anti-tumor agents. However, these drugs generally encounter problems that their specificity is low and side-effects are serious. On the other hand, many tumor cell growth inhibitors have been found in tissue culture cells. These inhibitors could be such anti-tumor agents that would be highly specific and would have minimized side-effects. Representative examples of such inhibitors are interferon, lymphotoxin and tumor necrosis factor (TNF). Recently, a tumor cell cytotoxic factor obtained from human fibroblast and a tumor cell growth inhibitor obtained from human lung cancer cells are reported in Japanese Patent KOKAI Nos. 1-148197 and 1-187094, respectively.

Some cell growth inhibitors are isolated also from the fibroblastic 3T3 cell line established from the cells obtained from Swiss fetal mice. For example, Natraj et al. has reported that a growth inhibitor was obtained from the cell surface of 3T3 cells in the stationary phase, cf., Proc. Natl. Acad. Sci. U.S.A., 75, 6115–6119 (1978). Harel et al. has reported that a growth inhibitor having a molecular weight of 40 kDa was obtained from the culture supernatant of 3T3 cells, see J. Cell. Physiol., 119, 101–106 (1984), ibid., 123, 139–143 (1985). However, these growth inhibitors all fail to show any significant inhibitory action against tumor cells, as is known in the art.

The present inventors previously succeeded in isolating, from the culture supernatant of 3T3 cell-derived cell line, novel tumor cell growth inhibitors having an activity of inhibiting the growth of tumor cells, which was filed as Japanese Patent Application No. 3-11950.

The tumor cell growth inhibitors exhibit a potent growth inhibition activity against human promyelogenous leukemia cells or human uterine cervical cancer-derived cells and are expected to be effective for the treatment of cancer.

For use as new carcinostatic agents, it is required to supply the tumor cell growth inhibitors in a sufficient amount. It is thus desired to develop a method for production available with industrial advantages.

DISCLOSURE OF INVENTION

The present inventors have brought attention to recombinant DNA technique applicable to the process for production of the tumor cell growth inhibitors in an industrially efficient way, and made investigations on cloning of cDNA encoding the tumor cell growth inhibitors. Succeeded by recombinant DNA technique in obtaining DNA fragments encoding the inhibitors which can be used for production of the inhibitors, the present invention has been accomplished.

That is, the present invention relates to DNA fragments encoding the tumor cell growth inhibitors, which has nucleotide sequence shown by formula (1):

```
                                             27
GTG CAG ATT ACA AAG TGT AGT TCT GAC ATG
                                             54
GAC GGC TAC TGC TTG CAT GGC CAG TGC ATC
                                             81
TAC CTG GTG GAC ATG AGA GAG AAA TTC TGC
                                            108
AGA TGT GAA GTG GGC TAC ACT GGT CTG CGA
TGT GAG CAC X . . . . . . . . . . . (1)
``` wherein X represents TTC TTT CTA or TTC.

BRIEF DESCRIPTION OF DRAWINGS

FIG. 3 shows oligonucleotides (1) through (11) used as primers in the PCR method.

FIG. 5 is an outline of the DNA fragment obtained by the PCR method.

FIG. 6 shows a nucleotide sequence of the DNA fragment encoding a part of P-1and the translated amino acid sequence.

FIG. 7 shows a nucleotide sequence of the DNA fragment encoding the C-terminal region of P-1 and the translated amino acid sequence.

FIG. 8 shows a nucleotide sequence of the DNA fragment encoding the N-terminal region of P-1 and the amino acid sequence translated therefrom.

FIG. 10 shows a nucleotide sequence of the DNA fragment encoding the entire region of P-1 and the amino acid sequence translated therefrom.

BEST MODE FOR CARRYING OUT THE INVENTION

The two tumor cell growth inhibitors are involved in the present invention, one inhibitor being encoded by the DNA fragment having a nucleotide sequence of formula (1) wherein X is TTC TTT CTA (hereinafter sometimes abbreviated as P-1), another being encoded by the DNA fragment having a nucleotide sequence of formula (1) wherein X is TTC (hereinafter sometimes abbreviated as P-2).

These inhibitors can be isolated and purified from the culture supernatant of the established cell line NIH3T3-sf, which is obtained by subculture from NIH3T3 cells (J. Virol., 4, 549 (1969)), one of fibroblastic 3T3 cell lines established from Swiss fetal mice, see Japanese Patent Application No. 3-11950.

The inhibitors P-1 and P-2 are peptides having an amino acid sequence shown by formula (2) below:

```
 1    2    3    4    5    6    7    8    9
Val—Gln—Ile—Thr—Lys—Cys—Ser—Ser—Asp—

10   11   12   13   14   15   16   17   18
Met—Asp—Gly—Tyr—Cys—Leu—His—Gly—Gln—

19   20   21   22   23   24   25   26   27
Cys—Ile—Tyr—Leu—Val—Asp—Met—Arg—Glu—

28   29   30   31   32   33   34   35   36
Lys—Phe—Cys—Arg—Cys—Glu—Val—Gly—Tyr—

37   38   39   40   41   42   43
Tyr—Gly—Leu—Arg—Cys—Glu—His—Y ........ (2)
``` wherein Y represents Phe-Phe-Phe-Leu or Phe.

The inhibitor P-1 is a peptide having an amino acid sequence shown by formula (2) wherein Y is Phe-Phe-Leu, and the inhibitor P-2 is a peptide having an amino acid sequence shown by formula (2) wherein Y is Phe.

Cloning of cDNA encoding the inhibitor P-1 or P-2 is performed as described below.

From NIH3T3-sf cells which are the established cell line, mRNA is extracted, adsorbed onto oligo dT cellulose column and then eluted to purify the adsorbed mRNA. These procedures may be carried out using a commercially available kit for mRNA extraction.

Using the thus purified mRNA as a template and oligo dT as a primer, cDNA is synthesized by reverse transcriptase and DNA polymerase. The terminus of this cDNA is rendered blunt in a conventional manner and bound to, e.g., EcoRI adapter. The product is then blended with, e.g., lambda phage gt10-EcoRI arm to bind to each other, using T4 DNA ligase. A vector containing cDNA is thus constructed. Next, phage particles are formed by the in vitro packaging method (Hohn et al., Proc. Natl. Acad. Sci. U.S.A., 74, 3259 (1977)) using the vector-bound cDNA as a template to obtain cDNA library.

Using this cDNA library as a template, various DNA fragments considered to encode the inhibitor P-1 or P-2 are amplified by the PCR method (Saiki et al., Science, 230, 1350 (1985)). Based on the thus obtained DNA fragments, the nucleotide sequence of the desired DNA fragment encoding the inhibitor P-1 or P-2 can be determined.

More specifically, the cloning can be made following the procedures shown in the embodiments described below.

Figure 2:
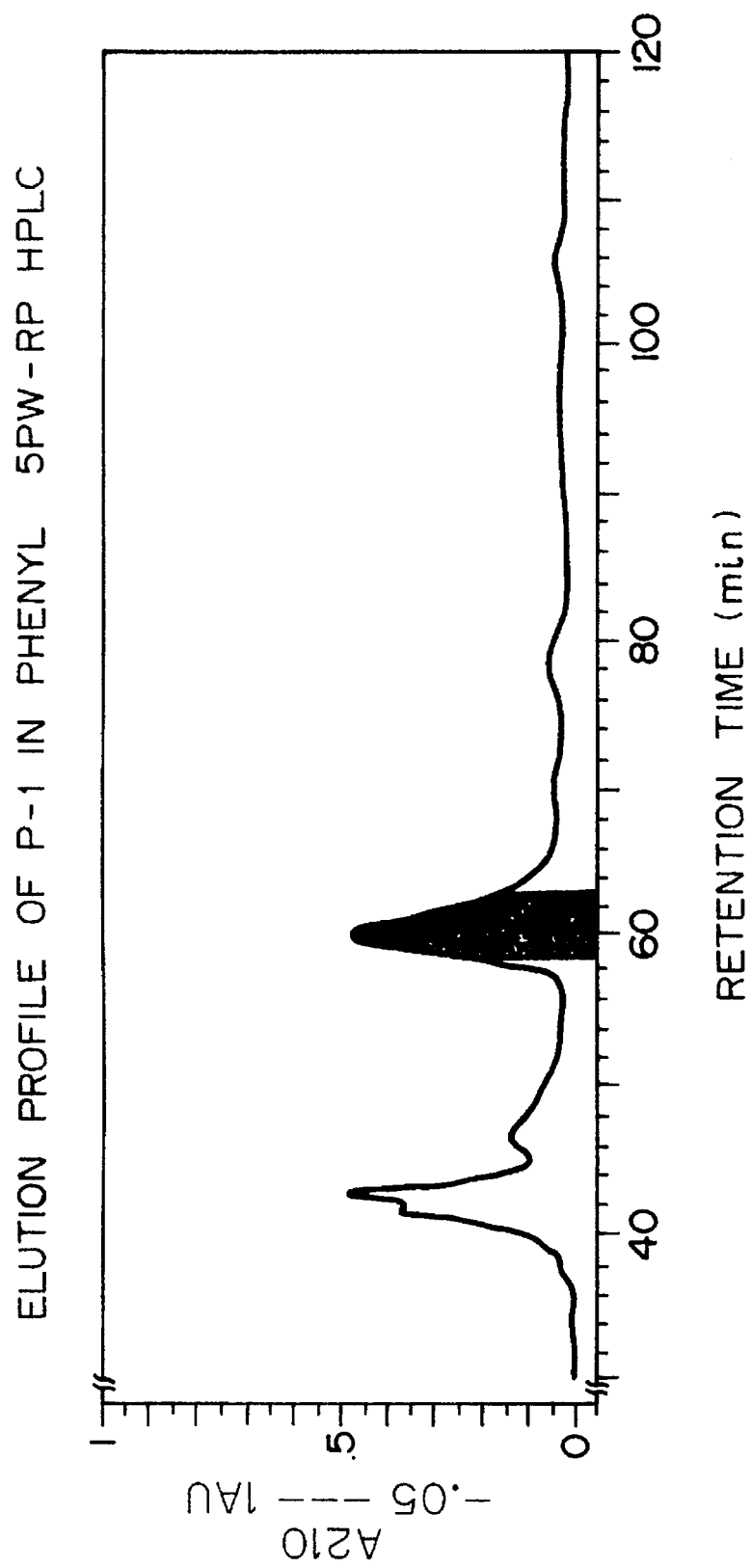
FIG. 2 is a graph showing elution profile of phenyl 5PW-RP reversed phase HPLC of tumor cell growth inhibitor P-2 which is the subject of the present invention.

Firstly, a DNA fragment which is considered to encode the inhibitor P-1 is amplified by the PCR method, using as the 5'-end primer the oligonucleotide (1) shown in FIG. 3 and having the nucleotide sequence corresponding to 1 to 6 residues of the amino acid sequence and as the 3'-end primer the oligonucleotide (2) shown in FIG. 3 and having the complementary sequence to the nucleotide sequence which corresponds to 41 to 46 amino acid sequence, in the amino acid sequence of the inhibitor P-1 shown in FIG. 2. In this case, the cDNA library described above is used as a template. Next, a DNA fragment which is considered to encode a part of the inhibitor P-1 is further amplified by the PCR method, using as a template the amplified DNA fragment, which is named the reaction product 1 and, using the oligonucleotide (1) as the 5'-end primer and as the 3'-end primer the oligonucleotide (3) shown in FIG. 3 and having the complementary sequence to the nucleotide sequence corresponding to 32 to 37 amino acid residues.

The amplified DNA fragment, which is named the reaction product 2, is separated by electrophoresis. The thus obtained DNA fragment is cloned to, e.g., single stranded phage M13mp18RF (Messing et al., Gene, 33, 103 (1985)) and the nucleotide sequence of the DNA fragment is determined by the dideoxy chain terminator method (Sanger, E. et al., Proc. Natl. Acad. Sci. U.S.A., 74, 5463 (1977)). FIG. 6 shows the nucleotide sequence of the DNA fragment thus determined, namely, the DNA fragment encoding the amino acid sequence of 1 to 36 residues in the inhibitor P-1.

Based on the thus determined nucleotide sequence, a DNA fragment which is considered to encode the C-terminal region of the inhibitor P-1 is further amplified by the PCR method. That is, the DNA fragment is amplified in a manner similar to the procedure described above, using as the 5'-end primer, e.g., the oligonucleotide (4) (see FIG. 3) corresponding to 18 to 37 bases and the oligonucleotide (5) (see FIG. 3) corresponding to 68 to 87 bases, and as the 3'-end primer the oligonucleotide (6) (see FIG. 3) having the complementary nucleotide sequence to the sequence near the EcoRI digestion site of λgt10 used for producing the cDNA library, in the nucleotide sequence shown in FIG. 6; in this case, the cDNA library is used as a template. Based on the thus obtained DNA fragment, which is named the reaction product 4, the nucleotide sequence is determined as described above. FIG. 7 shows the nucleotide sequence of the DNA fragment containing the C-terminal region of the inhibitor P-1.

Next, the nucleotide sequence of the DNA fragment encoding the N-terminal region of the inhibitor P-1 is determined in a similar manner. That is, the DNA fragment is amplified by the PCR method using the oligonucleotides (7), (8) and (9) shown in FIG. 3 as primers. Using the so obtained DNA fragment, which is named the reaction product 5, the nucleotide sequence is determined in a similar manner. FIG. 8 shows the nucleotide sequence of the DNA fragment containing the N-terminal region of the inhibitor P-1.

Based on the nucleotide sequences of various DNA fragments thus obtained and the amino acid sequence of the inhibitor P-1, the nucleotide sequence of the DNA fragment encoding the entire region of the inhibitor P-1 can be determined, see FIG. 10.

Based on the nucleotide sequence so determined, the DNA fragment encoding the inhibitor P-1 is cloned to obtain the DNA fragment in large quantities.

That is, the DNA fragment is amplified by the PCR method, using as the 5'-end primer the oligonucleotide (10) shown in FIG. 3 and corresponding to the 5'-end region of the nucleotide sequence shown in FIG. 10 or by formula (1) and as the 3'-end primer the oligonucleotide (11) shown in FIG. 3 and having the complementary sequence to the nucleotide sequence corresponding to the 3'-end region; in this case, the cDNA library prepared as described above is used as a template. The amplified DNA fragment, which is named the reaction product 6, is separated by electrophoresis. The thus obtained DNA fragment is then cloned to, e.g., single stranded phage M13mp18RF at the SmaI site thereof, as described above. The nucleotide sequence of the DNA fragment of formula (1) which encodes the inhibitor P-1 can thus be obtained.

Figure 4:
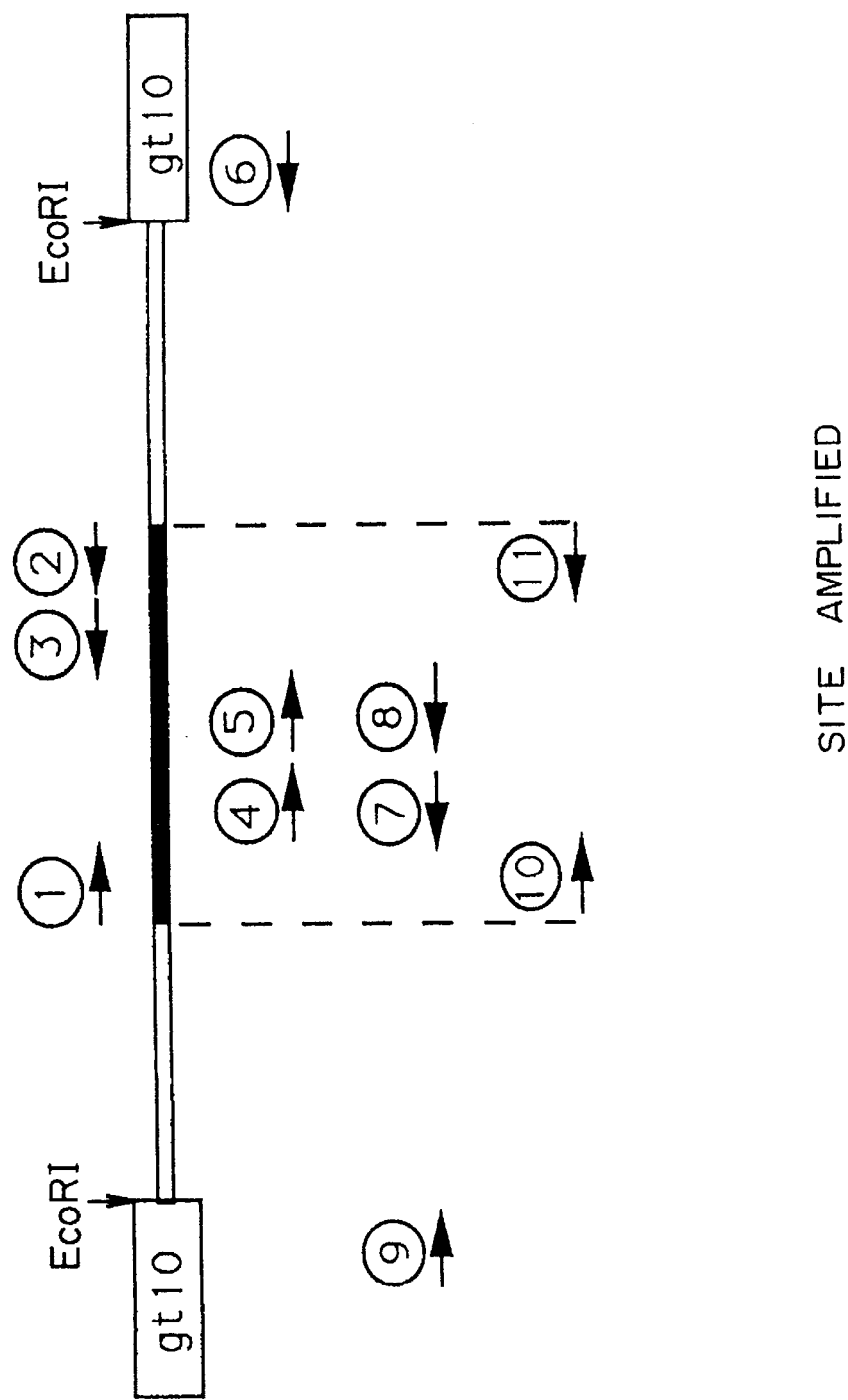
FIG. 4 briefly shows the amplified site of DNA fragment amplified by the PCR method.

The sites at which various DNA fragments are amplified as described above by the PCR method using the oligonucleotides (1) to (11) as the primers are illustratively shown in FIG. 4. The various DNA fragments so amplified, namely, the DNA fragments of the reaction products 2, 4, 5 and 6 described above, are illustratively shown in FIG. 5.

The DNA fragment encoding the inhibitor P-2 can be obtained in a similar manner. For example, the DNA fragment is amplified by the PCR method, using as the 5'end primer the oligonucleotide (10) corresponding to the 5'-end region of the nucleotide sequence shown in FIG. 10 and as the 3'-end primer the oligonucleotide (11) having the complementary sequence (5'-GAAGTGCTCACATCGCA-GAC-3') to the nucleotide sequence of 113 to 132 bases at the 3'-end shown in FIG. 10; in this case, the cDNA library described above is used as a template. The amplified DNA fragment is then separated by electrophoresis as described above. The thus obtained DNA fragment is cloned to obtain the DNA fragment encoding the inhibitor P-2.

The cloning of cDNA encoding the inhibitor P-1 and the inhibitor P-2 may also be effected as follows.

The oligonucleotide deduced from the amino acid sequence shown by formula (2) is chemically synthesized and labelled with an isotope. Using the labelled oligonucleotide as a probe, the desired cDNA is isolated, e.g., from the cDNA library described above, by the plaque hybridization technique, and then cloned in a conventional manner.

Alternatively, the DNA fragment having the nucleotide sequence of formula (1) which encodes the inhibitor P-1 or P-2 may also be chemically synthesized by known methods, e.g., by the triester phosphate method (Letsinger et al., J. Am. Chem. Soc., 91, 3350 (1969)).

Hereinafter the present invention will be described below in more detail, by referring to the examples and the reference examples.

Reference Example Isolation and purification of inhibitors P-1 and P-2 as well as the determination of their structures 1. Preparation of 3T3 cell-derived established cell line NIH3T3 cells were subcultured in DF medium (Dulbecco's modified MEM:HamF-12=1:1) containing 10% calf fetal serum and then cultured in DF containing 5 μg/ml of insulin, 5 μg/ml of transferrin and $2\times10^{-8}$M selenate to obtain proliferated clones.

From the clones, a clone which grew only in DF medium was selected and subcultured to establish the cell line. The thus obtained cell line was named NIH3T3-sf. The incubation was performed at 37° C. under the gaseous phase of 5% $CO_2$. The subculture was carried out by diluting to 2-fold at the time when the culture cells reached sub-confluence. The medium was prepared from a conditioned medium and a fresh medium in a proportion of 50%:50% and the so prepared medium was provided for use.

2. Preparation of serum-free culture supernatant of NIH3T3-sf cells

NIH3T3-sf cells were cultured in DF medium containing 10% calf fetal serum. When the cultured cells reached confluence, the medium was removed and washed once with PBS(−) ($KCl$:0.2 g, $KH_2PO_4$:0.2 g, NaCl:8 g, $Na_2HPO_4$: 1.150 g/l) followed by incubation in DF medium for 48 hours. After the medium was removed, incubation was performed in a fresh DF medium for 96 to 120 hours. The medium was exchanged with fresh medium every 96 to 120 hours to collect 100 liters. The collected medium was centrifuged at 2000 r.p.m. for 10 minutes to recover the supernatant.

3. Purification

1) Q-Sepharose column chromatography:

Using Perikon cassette system (ultrafiltering membrane system, molecular weight for fractionation: 1000), 100 liters of the culture supernatant collected was concentrated to about 50 times. The concentrate was subjected to salting-out with 90% ammonium sulfate saturation followed by centrifugation at 8000×g for 60 minutes. The thus obtained precipitates were dissolved in 20 mM Tris-HCl buffer (pH 7.4) and the solution was dialyzed the same buffer. Next, the dialysate was added to Q-Sepharose column (Pharmacia, φ5 cm×5 cm), which had been previously equilibrated with the same buffer, to collect the non-adsorbed fraction and the fraction washed.

Conditions for the elution are as follows.

Flow rate: 8 ml/min

Fractionation: 2 ml/tube

Eluant: 20 mM Tris-HCl buffer (pH 7.4)

2) S-Sepharose column chromatography:

After adjusting pH to 5.0 with acetic acid, the non-adsorbed fraction was added to S-Sepharose column (Pharmacia, φ2.5 cm×6 cm), which had been previously equilibrated with 20 mM acetate buffer (pH 5.0). The active component was adsorbed onto the column. Elution with 20 mM Tris-HCl buffer (pH 7.4) to obtain the active fraction. Conditions for the elution were as follows.

Flow rate: 0.85 ml/min

Fractionation: 4 ml/tube

Eluant: 20 mM Tris-HCl buffer (pH 7.4)

3) Hydroxyapatite column chromatography HPLC:

After adjusting pH of the active fraction eluted out of the S-Sepharose column to 6.0 with acetic acid, the active fraction was added to hydroxyapatite column (Asahi Optical Co., Ltd., φ7.5 mm×10 cm), which had been previously equilibrated with 20 mM acetate buffer (pH 6.0). The non-adsorbed fraction was thus collected. Conditions for the elution were as follows.

Flow rate: 1 ml/min

Fractionation: 1 ml/tube

Eluant: 20 mM acetate buffer (pH 6.0)

4) TSK gel CM-3SW column chromatography HPLC:

After adjusting pH of the active fraction to 5.0 with acetic acid, the fraction was poured onto TSK gel CM-3SW column (Toso, φ7.5 mm×7.5 cm), which had been previously equilibrated with 20 mM acetate buffer (pH 5.0) containing 5% acetonitrile ($CH_3CN$).

Conditions for the elution were as follows.

Flow rate: 1 ml/min

Fractionation: 1 ml/tube

Eluant:
  (A) 20 mM acetate buffer (pH 5.0)/5% $CH_3CN$
  (B) 20 mM acetate buffer (pH 5.0)/5% $CH_3CN$/ 0.2M NaCl linear density gradient of A→B (120 minutes)

The activity was noted in the two fractions which were eluted in NaCl concentrations of 86 mM (P-1) and 100 mM (P-2).

Figure 1:
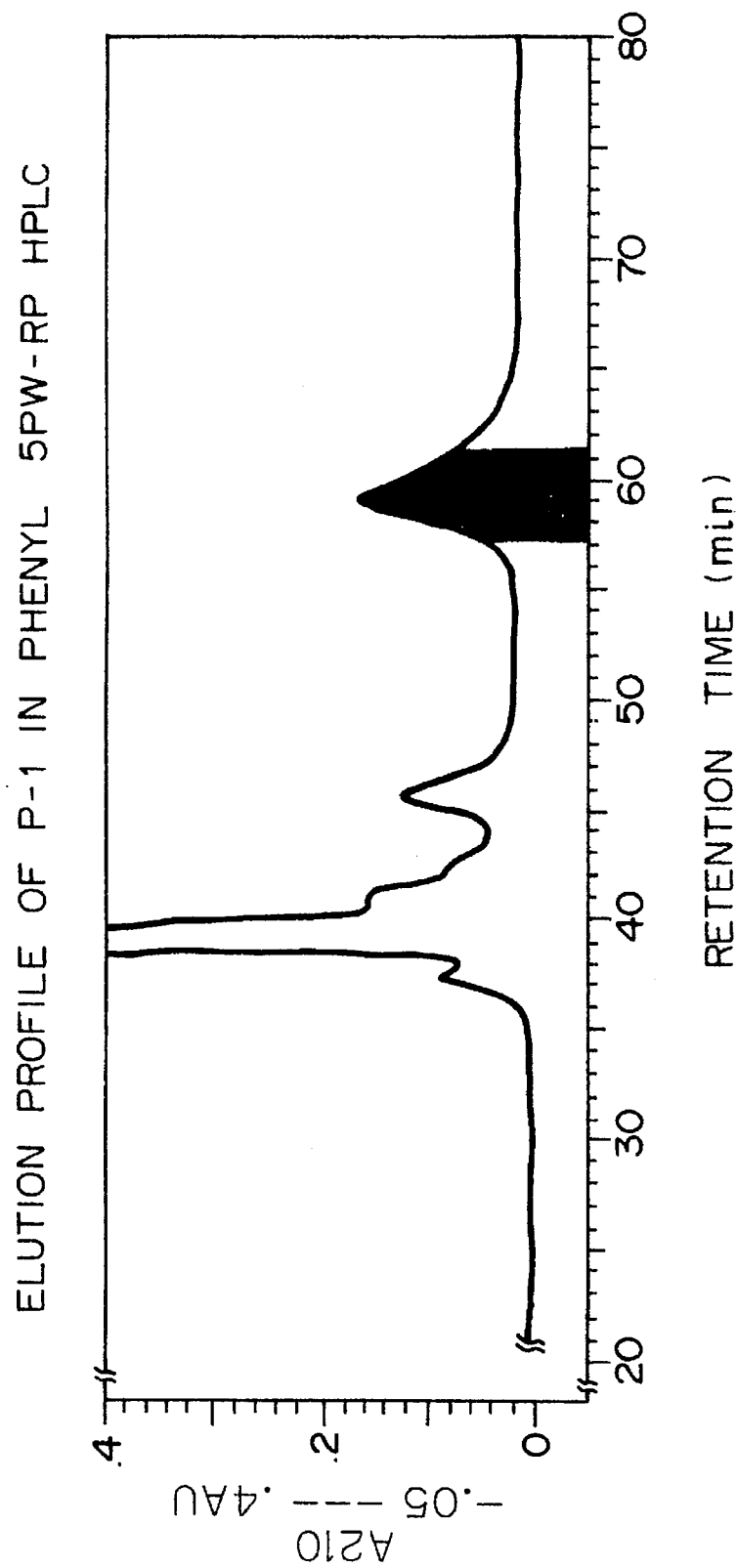
FIG. 1 is a graph showing elution profile of phenyl 5PW-RP reversed phase HPLC of tumor cell growth inhibitor P-1, which is the subject of the present invention.

5) Phenyl 5PW-RP reversed phase column chromatography HPLC:

The active fractions obtained in the CM-3SW HPLC step were poured onto Phenyl-5PWRP column (Toso, φ4.6 mm×7.5 cm), respectively, which had been previously equilibrated with 20 mM acetate buffer (pH 7.4) containing $CH_3CN$. Elution was effected by eluting with 20% $CH_3CN$-containing 5 mM phosphate buffer (pH 7.4) for 20 minutes and then by linear density gradient for 80 minutes using the same buffer containing 20% to 40% $CH_3CN$. The flow rate was 1 ml/min and fractionation was performed at 2 ml/tube. P-1 and P-2 were eluted at the positions of 59 to 60 minutes, and 60 to 61 minutes in retention time, respectively, see FIGS. 1 and 2.

5. Determination of amino acid sequences

The amino acid sequences of the two products purified were determined by the automated Edman degradation method using a gaseous protein sequencer (Model 470A, Applied Bio-Systems Co., Ltd.). As described above, the determination revealed that P-1 has an amino acid sequence of formula (2) wherein Y is Phe-Phe-Leu and P-2 has an amino acid sequence of formula (2) wherein Y is Phe.

EXAMPLE

Isolation of DNA fragments encoding P-1 and P-2 and determination of the nucleotide sequences 1) Production of cDNA library of NIH3T3-sf cells
(1) Preparation of NIH3T3-sf cells:

NIH3T3-sf cells were cultured in the manner shown in Reference Example 2. That is, the cells were cultured at 37° C. in 10% calf fetal serum-containing DF medium in 5% $CO_2$. When the cells reached confluence, the medium was removed and washed once with PBS (−) followed by incubation in DF medium for 120 hours.

(2) Extraction of mRNA from NIH3T3-sf cells:

The medium of the cells cultured in the manner shown in (1) above was removed. After washing once with PBS (−), PBS (−) was supplemented. The cells were then scraped out with a cell scraper and collected in a conical tube. After centrifugation at 1500×g for 5 minutes at room temperature, PBS (−) was added to suspend the cells therein. The suspension was again centrifuged to obtain the precipitates. From the precipitates, mRNA was extracted using mRNA Extraction Kit (manufactured by Invitrogen Co., Ltd.). Following this procedure, 19.2 µg of mRNA was purified from $2 \times 10^8$ cells.

(3) Synthesis of cDNA:

Using the mRNA prepared in (2) as a template, cDNA was synthesized using oligo dT as a primer, by the use of cDNA Synthesis Kit (manufactured by Pharmacia). Following this procedure, 1.0 µg of cDNA was synthesized from 1.9 µg of mRNA.

(4) Binding of cDNA to vector:

cDNA Cloning Kit (manufactured by Pharmacia) was used. That is, after the terminus of the cDNA synthesized in (3) above was rendered blunt with DNA polymerase large fragment of E. coli and four deoxynucleotide triphosphates, EcoRI adapter was bound thereto.

The cDNA was mixed with lambda phage gt10-EcoRI arm (manufactured by Strategene Co., Ltd.) and bound to each other using T4 DNA ligase.

(5) In vitro packaging:

Using the vector-bound cDNA shown in (4) as a template, phage particles were produced using in vitro packaging kit (manufactured by Amersham Co., Ltd.) to prepare cDNA library.

2) Amplification of DNA fragment encoding a part of P-1 by the PCR method and analysis of nucleotide sequence (1) Amplification of DNA fragment encoding a part of P-1:

Based on the amino acid sequence of P-1 determined in Reference Example: 5, oligonucleotides corresponding to the amino acid sequences of the N-terminal and C-terminal regions were synthesized. Using these oligonucleotides as primers, the DNA fragment encoding a part of P-1 was amplified by the PCR method (Saiki et al., Science, 230, 1350 (1985)), in which the cDNA library prepared in 1) above was used as a template. In the PCR reaction, Gene Amp PCR reagent Kit with AmpliTaq DNA Polymerase (manufactured by Perkin-Elmer Cetus Instrument Co., Ltd.) and DNA Thermal Cycler (manufactured by Perkin-Elmer Cetus Instrument Co., Ltd.) were used.

That is, oligonucleotides having the following nucleotide sequences in the amino acid sequence of P-1 shown in formula (2) were synthesized, see FIGS. 3 and 4:

oligonucleotide (1) having the nucleotide sequence corresponding to the amino acid sequence of 1 to 6 residues (Val-Gln-Ile-Thr-Lys-Cys):

5'-GTNCARATHACNAARTG-3' wherein N is A, T, G or C; R is A or G; H is A, C or T: a mixture of the oligonucleotides wherein N, R and H represent the respective bases was used;

oligonucleotide (2) having the complementary sequence to the nucleotide sequence corresponding to the amino acid sequence of 41 to 46 residues (Cys-Glu-His-Phe-Phe-Leu):

5'-ARRAARAARTGYTCRCA-3' wherein Y is C or T; a mixture of the two oligonucleotides wherein Y is C or T was used; oligonucleotide (3) having the complementary sequence to the nucleotide sequence corresponding to the amino acid sequence of 32 to 37 residues (Cys-Glu-Val-Gly-Thy-Thr):

5'-GTRTANCCNACYTCRCA-3'

Next, the DNA fragment encoding a part of P-1 was amplified by the following procedures.

heating 10 µl of the cDNA library prepared in 1)–(5) above at 100° C. for 10 minutes
↓
ice cooling
↓
adding thereto:

oligonucleotide (1) in a final
concentration of 10 µM
oligonucleotide (2) in a final
concentration of 10 µM
0.5 µl (2.5 units) of AmpliTaq Polymerase
(manufactured by Perkin-Elmer Cetus
Instrument Co., Ltd. ) and,
distilled water to make the whole volume
100 µl
↓
adding thereto:

10 µl of 10 × Buffer A (100 mM Tris-HCl, pH
8.3, 500 mM KCl, 15 mM $MgCl_2$, 0.01% (w/v)
gelatin) and,
16 µl of 1.25 mM dNTP (wherein N is A, T, G
or C)
↓
heating at 94° C. for 1 minute
↓
heating at 40° C. for 2 minutes
↓
heating at 72° C. for 3 minutes
(30 repetitions of the heating procedure)
↓
reaction product 1
10 µl of the reaction product 1
↓
adding thereto:

oligonucleotide (1) in a final
concentration of 10 µM
oligonucleotide (3) in a final
concentration of 10 µM
0.5 µl (2.5 units) of AmpliTaq Polymerase
(manufactured by Perkin-Elmer Cetus
Instrument Co., Ltd.)
and distilled water to make the whole
volume 100 µl
↓

-continued adding thereto:

10 μl of 10 × Buffer A and
16 μl of 1.25 mM dNTP (wherein N is A, T, G or C)
↓
heating at 94° C. for 1 minute
↓
heating at 40° C. for 2 minutes
↓
heating at 72° C. for 3 minutes
(30 repetitions of the heating procedure)
↓
reaction product 2 (cf. FIG. 5)

(2) Cloning of DNA fragment encoding a part of P-1:

The reaction product 2 was subjected to electrophoresis on 5% polyacrylamide gel, whereby a band stained with ethydium bromide was confirmed around 110 base pairs. The band was cut out and cloned to single stranded phage M13mp18RF at the SmaI site. The cutting-out of the band and extraction of DNA were carried out as follows, according to T. Maniatis et al., Molecular Cloning, page 178 (1982).

dissolving DNA in 7 μl of H₂O
↓
adding to the solution:
1 μl of 10 × Buffer B (0.5M Tris-HCl, pH
7.8, 0.1 M MgCl₂, 10 mM DTT)
1 μl (5 units) of Klenow fragment and,
1 μl of 10 mM dNTP wherein N is A, T, G or C
↓
heating at 22° C. for 1 hour
↓
heating at 68° C. for 10 minutes
↓
ethanol precipitation
↓
dissolving the precipitates in 7 μl of distilled water
↓
adding to the solution:
1 μl of 10 × Buffer C (0.5M Tris-HCl, pH
7.6, 0.1M MgCl₂, 0.1M DTT)
1 μl (5 units) of 10 mM ATP and,
1 μl of T4 polynucleotide kinase
↓
heating at 37° C. for 1 hour
↓
heating at 68° C. for 10 minutes
↓
phenol extraction
↓
ethanol precipitation
↓
dissolving the precipitates in 7 μl of distilled water
↓
adding to the solution:
1 μl of 10 × Buffer D (0.66M Tris-HCl, pH
7.6, 50 mM MgCl₂ 50 mM DTT, 10 mM ATP)
1 μl (350 units) of T4 DNA ligase and,
1 μl (0.5 μg) of M13mp18RF digested with SmaI
↓
heating at 15° C. for 15 hours This DNA was transfected to *E. coli* JM109 (C. Yanisch-Perrson et al., Gene. 33, 103 (1985)) treated with calcium chloride (Maniatis et al., Molecular Cloning, 250 (1982)) and then seeded on L agar medium (trypton: 10 g, yeast extract: 5 g, sodium chloride: 10 g, agar powders: 15 g/l). To 3 ml of soft agar medium (trypton: 10 g, yeast extract: 5 g, sodium chloride: 10 g, agarose: 7.5 g/l) kept at 45° C., was added 0.1 ml of *E. coli* JM109 independently incubated. The mixture was laid on the L agar medium plate and incubated at 37° C. to obtain a plaque.

(3) Analysis of nucleotide sequence:

The plaque prepared in 2)-(2) was adsorbed onto strain JM109 followed by incubation. From the culture supernatant single stranded DNA was extracted according to the method of Messing et al., Gene, 33, 103 (1985). Using 7-Deaza-Sequencing Kit (Toyobo Co., Ltd.), the nucleotide sequence was determined by the dideoxy chain terminator method (Sanger, F. et al., Proc. Natl. Acad. Sci. U.S.A., 74, 5463 (1977)), cf. FIG. 6. Translation of the nucleotide sequence into amino acids reveals that the DNA fragment encodes a part (1 to 36 amino acid residues) of P1.

3) Amplification of DNA fragment encoding the C-terminal region of P-1 by the PCR method and analysis of its nucleotide sequence (1) Amplification of the DNA fragment encoding the C-terminal region of P-1:

Based on the nucleotide sequence determined in 2)–(3), oligonucleotides were synthesized. Using these oligonucleotides and a part of λgt10 as primers, the DNA fragment encoding the C-terminal region of P-1 was amplified by the PCR method in which the cDNA library prepared in 1)–(5) above was used as a template. That is, the following oligonucleotides were synthesized, see FIGS. 3 and 4.

oligonucleotide (4) corresponding to 18 to 37 bases, in the nucleotide sequence shown in FIG. 4;

oligonucleotide (5) corresponding to 68 to 87 bases, and oligonucleotide (6) having the nucleotide sequence around the EcoRI digestion site of λgt10.

Next, the DNA fragment encoding the C-terminal region of P-1 was amplified by the procedure shown below.

heating 10 μl of the cDNA library prepared in 1)-
(5) above at 100° C. for 10 minutes
↓
ice cooling
↓
adding thereto:

oligonucleotide (4) in a final
concentration of 1 μM
oligonucleotide (6) in a final
concentration of 1 μM
0.5 μl (2.5 units) of AmpliTaq Polymerase
(manufactured by Perkin-Elmer Cetus
Instrument Co., Ltd.) and,
distilled water to make the whole volume
100 μl
↓
adding thereto 10 × Buffer A and 16 μl of 1.25 mM
dNTP (wherein N is A, T, G or C)
↓
heating at 94° C. for 1 minute
↓
heating at 52° C. for 2 minutes
↓
heating at 72° C for 3 minutes
(30 repetitions of the heating procedure)
↓
reaction product 3
10 μl of the reaction product 3
↓
adding thereto:

oligonucleotide (5) in a final
concentration of 1 μM
oligonucleotide (6) in a final
concentration of 1 μM
0.5 μl (2.5 units) of AmpliTaq Polymerase
(manufactured by Perkin-Elmer Cetus
Instrument Co., Ltd.)

11
-continued and distilled water to make the whole
volume 100 µl
↓
adding thereto 10 × Buffer A and 16 µl of 1.25 mM
dNTP (wherein N is A, T, G or C)
↓
heating at 94° C. for 1 minute
↓
heating at 55° C. for 2 minutes
↓
heating at 72° C. for 3 minutes
(30 repetitions of the heating procedure)
↓
reaction product 4 (cf. FIG. 5)

(2) Cloning of DNA fragment encoding the C-terminal region of P-1:

The reaction product 4 was subjected to electrophoresis on 5% polyacrylamide gel, whereby a band stained with ethydium bromide was confirmed around 400 base pairs. The band was cut out and cloned to single stranded phage M13mp18RF at the SmaI site by the procedure shown in 2)-(2).

(3) Analysis of nucleotide sequence:

The nucleotide sequence was determined by the procedure shown in 2)–(3) above, see FIG. 7. Translation of the nucleotide sequence into amino acids reveals that the DNA fragment encodes the C-terminal region of P-1. That is, the DNA fragment encodes the C-terminal region corresponding to the underlined 24 to 46 amino acid residues in FIG. 7.

4) Amplification of DNA fragment encoding the N-terminal region of P-1 by the PCR method and analysis of its nucleotide sequence (1) Amplification of the DNA fragment encoding the N-terminal region of P-1:

Based on the nucleotide sequence of P-1 determined in 2)–(3), oligonucleotides were synthesized. Using these oligonucleotides and a part of λgt10 as primers, the DNA fragment encoding the N-terminal region of P-1 was amplified by the PCR method in which the cDNA library prepared in 1)–(5) above was used as a template.

That is, the following oligonucleotides were synthesized, see FIGS. 3 and 4.

- oligonucleotide (7) having the complementary sequence to the nucleotide sequence corresponding to 18 to 37 bases, in the nucleotide sequence of a part of P-1 shown in FIG. 4;
- oligonucleotide (8) having the complementary sequence to the nucleotide sequence corresponding to 68 to 87 bases, and
- oligonucleotide (9) having the nucleotide sequence around the EcoRI digestion site of λgt10.

Next, the DNA fragment encoding the N-terminal region of P-1 was amplified in a manner similar to the procedure shown in Example 2)–(1) except that the oligonucleotides (8) and (7) were used instead of the oligonucleotides (4) and (5), and the oligonucleotide (9) was used instead of the oligonucleotide (6). Finally the reaction product 5 was obtained, see FIG. 5.

(2) Cloning of DNA fragment encoding the N-terminal region of P-1:

The reaction product 5 was subjected to electrophoresis on 5% polyacrylamide gel, whereby a band stained with ethydium bromide was confirmed around 310 base pairs. The band was cut out and cloned to single stranded phage M13mp18RF at the SmaI site by the procedure shown in 2)-(2).

12

(3) Analysis of nucleotide sequence:

The nucleotide sequence was determined by the procedure shown in 2)–(3) above, see FIG. 8. Translation of the nucleotide sequence into amino acids reveals that the DNA fragment encodes the N-terminal region of P-1. That is, the DNA fragment encodes the N-terminal region corresponding to the underlined 1 to 12 amino acid residues in FIG. 8.

5) Verification of the nucleotide sequence of the DNA fragment encoding the entire region of P-1 by the PCR method In order to confirm the nucleotide sequence of the DNA fragment encoding the entire region of P-1 in the nucleotide sequences determined in 2) through 4) above, the oligonucleotide (10) corresponding to the 5'-end region and the oligonucleotide (11) having the complementary sequence to the nucleotide sequence corresponding to the 3'-end were synthesized, see FIGS. 3 and 4. Using these oligonucleotides as primers, the amplification and cloning of the DNA fragment encoding the entire region of P-1 were performed to analyze its nucleotide sequence.

(1) Amplification of the DNA fragment encoding the entire region of P-1:

heating 10 µl of the cDNA library prepared in 1)-
(5) above at 100° C. for 10 minutes
↓
ice cooling
↓
adding thereto:

oligonucleotide (10) in a final
concentration of 1 µM
oligonucleotide (11) in a final
concentration of 1 µM
0.5 µl (2.5 units) of AmpliTaq Polymerase
(manufactured by Perkin-Elmer Cetus
Instrument Co., Ltd.)
and distilled water to make the whole
volume 100 µl
↓
adding thereto 10 × Buffer A and 16 µl of 1.25 mM
dNTP (wherein N is A, T, G or C)
↓
heating at 94° C. for 1 minute
↓
heating at 55° C. for 2 minutes
↓
heating at 72° C. for 3 minutes
(30 repetitions of the heating procedure)
↓
reaction product 6 (see FIG. 5)

Figure 9:
FIG. 9 is a photograph showing the results of electrophoresis performed for separating the DNA fragment encoding the entire region of P-1.

(2) Cloning of DNA fragment encoding the entire region of P-1:

The reaction product 6 was subjected to electrophoresis on 5% polyacrylamide gel, whereby a band stained with ethydium bromide was confirmed around 138 base pairs, see FIG. 9. The band was cut out and cloned to single stranded phage M13mp18RF at the SmaI site by the procedure shown in 2)-(2).

(3) Analysis of nucleotide sequence:

The nucleotide sequence was determined by the procedure shown in 2)–(3) above, see FIG. 10. Translation of the nucleotide sequence into amino acids reveals that the amino acid sequence of the DNA fragment fully coincided with the entire amino acid sequence of P-1.

P-2 has such a structure that the 2 amino acid residues are deleted from the C-terminus of P-1. Accordingly, cloning of the DNA fragment encoding the entire region of P-2 can be performed by the procedures similar to those in 5) (1) and (2), using as primers oligonucleotide (10) corresponding to the 5'-end used in 5)-(1) and oligonucleotide (5'-GAAGT- GCTCACATCGCAGAC-3') having the complementary sequence to the nucleotide sequence corresponding to the 3'-end of the nucleotide sequence encoding P-2.

Industrial Applicability

As described above in detail, the present invention can provide the DNA fragments encoding the novel tumor cell growth inhibitors which are expected to be effective for the treatment of leukemia and uterus cervical cancer. By transfecting the DNA fragments to an expression vector in, e.g., *E. coli* and culturing the transformant obtained, the tumor cell growth inhibitors can be produced in large quantities. Therefore, the DNA fragments of the present invention enable to produce the tumor cell growth inhibitors in an industrial scale.

We claim:

1. A DNA fragment encoding a tumor cell growth inhibitor which has a nucleotide sequence shown by formula (1):

27
GTG CAG ATT ACA AAG TGT AGT TCT GAC ATG
                              54
GAC GGC TAC TGC TTG CAT GGC CAG TGC ATC
                              81
TAC CTG GTG GAC ATG AGA GAG AAA TTC TGC

108
AGA TGT GAA GTG GGC TAC ACT GGT CTG CGA
TGT GAG CAC X.......... (1)

wherein X represents TTC TTT CTA or TTC (SEQ ID NO:1 or SEQ ID NO:2).

* * * * *

UNITED STATES PATENT AND TRADEMARK OFFICE
CERTIFICATE OF CORRECTION

PATENT NO. : 5,523,391
DATED : June 4, 1996
INVENTOR(S) : KOMURASAKI et al

It is certified that error appears in the above-indentified patent and that said Letters Patent is hereby corrected as shown below:

Col. 6, line 56, after "containing" insert --5%--.

Signed and Sealed this

Fifteenth Day of April, 1997

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,523,391
DATED : June 4, 1996
INVENTOR(S) : KOMURASAKI et al

It is certified that error appears in the above-indentified patent and that said Letters Patent is hereby corrected as shown below:

On title page, insert the following:

--[30]   Foreign Application Priority Data
     December 5, 1991 [JP] Japan............... 3-321929--.

Signed and Sealed this

Twenty-fourth Day of June, 1997

Attest:

BRUCE LEHMAN

*Attesting Officer*        *Commissioner of Patents and Trademarks*